(12) United States Patent
Lorenz et al.

(10) Patent No.: US 6,697,654 B2
(45) Date of Patent: Feb. 24, 2004

(54) TARGETED INTERFERENCE SUBTRACTION APPLIED TO NEAR-INFRARED MEASUREMENT OF ANALYTES

(75) Inventors: Alexander D. Lorenz, Phoenix, AZ (US); Thomas B. Blank, Chandler, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/183,906

(22) Filed: Jun. 25, 2002

(65) Prior Publication Data

US 2003/0023148 A1 Jan. 30, 2003

Related U.S. Application Data

(63) Continuation-in-part of application No. 09/825,687, filed on Apr. 3, 2001, now Pat. No. 6,512,932, which is a continuation-in-part of application No. 09/359,191, filed on Jul. 22, 1999, now Pat. No. 6,280,381.

(51) Int. Cl.$^7$ ................................................ A61B 5/00
(52) U.S. Cl. ...................... 600/310; 600/473; 356/300; 250/339.11; 250/341.8
(58) Field of Search ................................ 600/310, 316, 600/322, 323, 473; 356/300, 319, 320, 326, 328; 250/339.01, 339.02, 339.06, 339.07, 339.11, 339.12, 340, 341.1, 341.2, 341.8

(56) References Cited

U.S. PATENT DOCUMENTS

| | | | | |
|---|---|---|---|---|
| 5,379,238 A | * | 1/1995 | Stark | 600/322 |
| 5,435,309 A | * | 7/1995 | Thomas et al. | 600/310 |
| 5,953,381 A | * | 9/1999 | Tsukahara | 375/346 |
| 6,175,602 B1 | * | 1/2001 | Gustafsson et al. | 375/346 |

\* cited by examiner

*Primary Examiner*—Eric F. Winakur
(74) *Attorney, Agent, or Firm*—Glenn Patent Group; Michael A. Glenn

(57) ABSTRACT

Methods and apparatus for estimating and removing spectral interference improve precision and robustness of non-invasive analyte measurement using Near-infrared (NIR) spectroscopy. The estimation of spectral interference is accomplished, either through multivariate modeling or discrete factor analysis, using a calibration set of samples in which the interference is orthogonal to the analyte signal of interest, or where the shape of the interference is known. Each of the methods results in a multivariate model in which the spectral interference is estimated for a new sample and removed by vector subtraction. Independent models based on classes of sample variability are used to collapse spectral interference and determine more accurately which model is best equipped to estimate the signal of interference in the new sample. Principal components analysis and other commonly known analytical techniques can be used to determine class membership.

68 Claims, 9 Drawing Sheets

TARGETED INTERFERENCE SUBTRACTION APPLIED TO NEAR-INFRARED MEASUREMENT OF ANALYTES

CROSS-REFERENCE TO RELATED APPLICATIONS

This application is a Continuation-in-part of U.S. patent application Ser. No. 09/825,687 filed on Apr. 3, 2001, now U.S. Pat. No. 6,512,937 which is a Continuation-in-part of U.S. patent application Ser. No. 09/359,191, filed on Jul. 22, 1999, now U.S. Pat. No. 6,280,381.

BACKGROUND OF THE INVENTION

1. Field of the Invention

The invention relates to the estimation and subtraction of interference from a NIR spectral measurement. More particularly, this invention relates to an apparatus and methods for determining targeted orthogonal interference and the development of models for removing unwanted spectral variation from a NIR measurement using techniques such as multivariate regression and discrete factor analysis.

2. Description of Related Art

Near-infrared (NIR) tissue spectroscopy is a promising noninvasive technology that bases measurements on the irradiation of a tissue site with NIR energy in the 700–2500 nanometer wavelength range. The energy is focused onto an area of the skin and propagates according to the scattering and absorption properties of the skin tissue. Therefore, the reflected or transmitted energy that escapes and is detected provides information about the tissue volume encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and analytes absorb light proportionally to their concentration through unique absorption profiles or signatures. The measurement of tissue properties, characteristics or composition is based on detecting the magnitude of light attenuation resulting from the respective scattering and/or absorption properties of the tissue sampled.

BIOLOGICAL ANALYTE MEASUREMENT

While global noninvasive measurement of biological constituents, such as glucose concentration, has been pursued through NIR spectroscopy, the reported success and product viability has been limited by the lack of a system for compensating for structural variations that occur over time in an individual and those that are present between individuals. This variation produces dramatic changes in the optical properties of the sampled tissue and inhibits the measurement of the signal related to the target constituents. See, for example, O. Khalil, Spectroscopic and Clinical Aspects of Non-invasive Glucose Measurements, *Clinical Chemistry*, Vol. 45, pp. 165–177, (1999) or J. Roe, B. Smoller, Bloodless Glucose Measurements, *Critical Reviews in Therapeutic Drug Carrier System*, Vol. 15 (3), pp. 199–241 (1998). With this problem being recognized, research has lead in the direction of developing analyte measurement models for individuals. Although variations in the optical properties of skin are reduced, the variations resulting from inconsistent sampling methods, for example, from coupling of the sample to the measurement device and slight variations in choice of sampling site, result in limited success. Furthermore, fluctuations in the physiological state of the individual, for example, changes in skin temperature, skin hydration levels, weight loss or weight gain, still limit the success of these models. Some of these variations can be reduced with refined experimental design and elaborate control strategies, but the resources required for such development are considerable. Therefore, variations in sampling technique and fluctuations in the physiological state of the individual are significant obstacles to overcome in the development of effective models for noninvasive measurement of analytes through NIR spectral absorbance.

The related application, T. Ruchti, T. Blank, A Multi-tier Approach to *Building Classification Models on Individuals for Noninvasive Measurement of Blood Glucose*, U.S. patent application Ser. No. 09/825,687 describes a method for substantially reducing spectral interference due to structural variations between individuals by classifying subjects according to major skin tissue characteristics prior to analyte measurement prediction. However, the subject application does not describe methods or apparatus to reduce variation across successive spectral measurements on the same individual.

In living subjects, inadequate sampling procedures and uncontrollable changes in skin tissue characteristics have been discovered to add significant interference to spectral measurements. This becomes increasingly important when attempting to estimate trace levels of analytes noninvasively. Therefore, an automated method for the estimation and removal of spectral interference prior to analyte measurement can provide increased measurement precision and accuracy.

SUMMARY OF THE INVENTION

The invention provides an apparatus and methods for modeling and removing targeted interfering signals from noninvasive spectral measurements such as NIR spectra. The invented methods are of utility in several areas, including analyte measurement and signal characterization. By grouping spectral measurements according to similar characteristics representing spectral variability, nonlinear variation is reduced and the determination and removal of interfering signals becomes easier, resulting in more accurate measurement of analytes. The invention finds particular application in the reduction of variation due to spectral interference across successive spectral measurements on the same individual.

A spectroscopic apparatus is used in conjunction with an optical interface to measure tissue properties and characteristics that are manifested spectrally and vary differently according to the sampled tissue and physiological changes in an individual.

Methods for determining the Net Analyte Signal (NAS) of a known specific spectral interference source utilize multivariate modeling and sample classification to remove unwanted spectral variation from future samples, thus yielding increased measurement precision and accuracy of analyte measurement.

A procedure for estimating known spectral interferences utilizes an empirically derived calibration model consisting of NIR tissue measurements from a set of exemplary samples and the measurements corresponding to a signal of interest that is to be removed. The model comprises a set of parameters and computer-generated code implemented to estimate the interfering signal of interest. The estimated signal reveals information relating to the property magnitude that the interference adds at any particular wavelength. Such properties include but are not limited to skin temperature, tissue hydration, sampled tissue site, pressure at apparatus interface, and day-to-day changes in an individual's physiological state.

The invention further provides a multi-tier approach to building classification models for specific interferences and its application to estimation of the true signal of interference in a new sample with greater accuracy.

DETAILED DESCRIPTION

Figure 1:
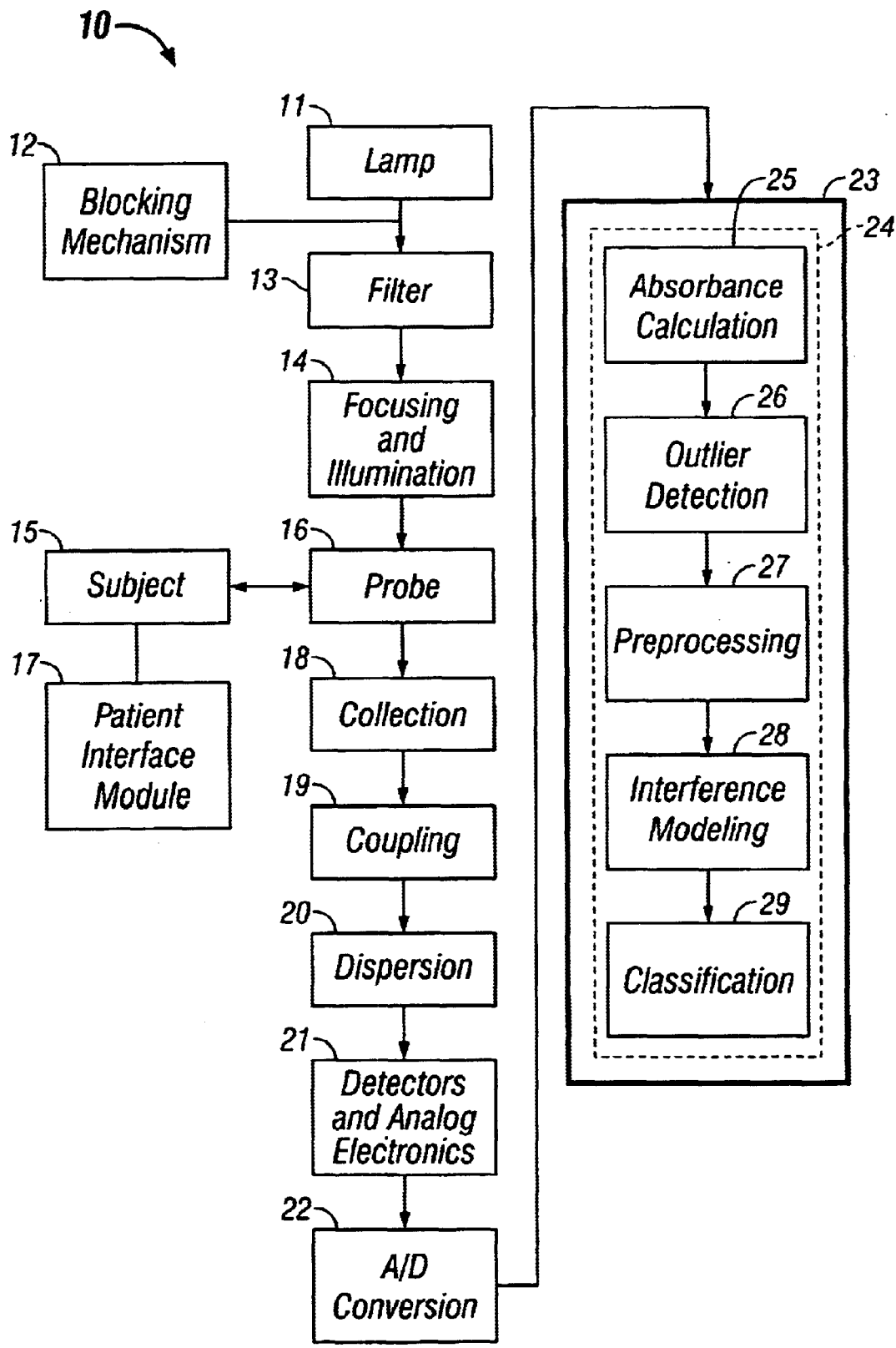
FIG. 1 provides a block diagram of a system for estimating and removing unwanted spectral variation from NIR spectral measurements according to the invention.

The invention provides an apparatus for measuring the infrared absorption by tissue irradiated with near-infrared energy and a procedure for non-invasively determining the signal of interference. For the purposes of the invention, the word "orthogonal" used herein below refers to two objects or vectors in multi-dimensional space that are orthogonal or nearly orthogonal with respect to each other.

Apparatus

The apparatus includes an energy source, a sensor element, a subject interface, a wavelength selection device and an analyzer. The energy source generates and transmits near-infrared energy in the wavelength range 700–2500 nanometers and consists of a device such as an LED array or a quartz halogen lamp. The sensing elements are detectors that are responsive to a predetermined set of targeted wavelengths. Wavelength separation may be achieved through the use of a monochromator, an interferometer or by means of successive illumination through the elements of an LED array. The subject interface provides a means of transmitting energy from the source to the target skin tissue measurement site and may include, for example a light pipe, fiber-optic probes, a lens system or a light directing mirror system. Energy is collected from the surrounding tissue areas in reflectance mode at an optimally determined distance(s) through the use of staring detectors or fiber optic probes. Alternately, energy is collected in a transmission mode through a skinfold, ear lobe, finger or other extremity. The collected light is converted to a voltage 15 and sampled through an analog-to-digital converter (ADC) 16 for analysis on a microprocessor-based system.

In a preferred embodiment the near-infrared apparatus 10 consists of a broadband source (such as a tungsten halogen lamp) 11, a band-pass filter 13 to limit the light intensity on the skin to the targeted wavelength range (700–2500 nm), a blocking mechanism 12 to allow the detection of detector dark current or baseline, a means for coupling the light to the skin such as a focusing system and fiber optics 14, a probe 16 for establishing contact with the skin by the focusing system and fiber optics 14 and fiber optics 18 for collecting light, a patient interface module 17 capable of precisely positioning and coupling the subject's 15 measurement site with minimal disturbance to the probe 16, a means for collecting light that is diffusely scattered or transmitted from the subject's tissue while avoiding specular reflectance, for example, one or more fiber optics 18, coupled 19 to an aperture such as a slit (not shown), through which collected light is delivered to a dispersive element 20 (e.g., a grating) that provides a spatial dispersion of collected light with respect to wavelength; a means for detecting the dispersed light at bands of wavelengths such as an array of detectors and associated electronic amplifiers 21; a means for digitizing the detected voltage such as an analog-to-digital converter 22 and a means of storing, processing and analyzing the detected voltage 23 at each wavelength, such as a microprocessor with associated memory. The spectrum is passed to the sample variability classification procedure 24 for processing. First, the absorbance is calculated 25 on the basis of the detected light through—$\log(R/R_o)$ where R is the reflected light and $R_o$, is the light incident on the sample determined by scanning a reference standard. Subsequent processing steps, described below, result in an absorbance spectrum with the selected interference removed or a message indicating an invalid scan. A block diagram of the integrated system is shown in FIG. 1.

Alternately, the measurement can be performed using existing commercially available NIR spectrometers, for example, a PERSTORP ANALYTICAL NIRS 5000 spectrometer, provided by PERSTORP ANALYTICAL, INC., Silver Springs Md. or a NICOLET MAGNA-IR 760 spectrometer, provided by THERMO NICOLET, INC of Madison Wis. Additionally, the measurement can be made by collecting reflected light off the surface of the skin or light transmitted through a portion of the skin, such as the finger or the ear lobe. Furthermore, the use of reflectance or transmittance can replace the preferred absorbance measurement.

General Spectral Intreference Estimation and Subtraction Procedure

The general procedure 24 for estimation and removal of spectral interference based on the measured spectrum, shown in FIG. 1, is implemented in a microprocessor 23 that automatically receives the measurement information from the ADC 22. The principal steps of the interference estimation procedure include outlier detection 26, preprocessing 27, interference modeling 28, and classification 29. The design of each step is performed on the basis of a calibration set of exemplary measurements. Herein below, the general steps of the procedure, detailed in the subsequent Design and Implementation Section, are summarized.

Measurement (25)

The measurement is a spectrum, denoted by the vector $m \in \Re^N$, of absorbance values pertaining to a set of N wavelengths $\lambda \in \Re^N$, that span the near infrared (700 to 2500 nm). A typical plot of m versus $\lambda$ is shown in to FIG. 3.

Outlier Detection (26)

The outlier detection procedure is a method for detecting invalid measurements through spectral variations that result from problems in the instrument, poor sampling of the subject or a subject outside the calibration set. The preferred method for the detection of spectral outliers is through a principal components analysis and an analysis of the resulting residuals. First, the spectrum, m, is projected onto five eigenvectors, contained in the matrix o, that were previously developed through a principal components analysis on a calibration set of exemplary absorbance spectra and stored in the computer system of the apparatus. The calculation is given by:

$$xpc_o = \sum_{k=1}^{5} mo_k, \tag{1}$$

and produces the 1 by 5 vector of scores, $xpc_o$ where $O_k$ is the $k^{th}$ column of the matrix o. The residual, q, is determined according to $$q = m - xpc_o o^T \tag{2}$$

and compared to three times the standard deviation of the expected residual of the calibration set. If greater, the sample is reported to be an outlier and the signal interference determination procedure is terminated.

Preprocessing (27)

Preprocessing includes operations such as scaling, normalization, smoothing, derivatives, filtering and other transformations that attenuate noise and instrumental variation without affecting the signal of interest. The preprocessed measurement, $x \in \Re^N$, is determined according to $$x = h(\lambda, m) \tag{3}$$

where $h: \Re^{N \times 2} \to \Re^N$, is the preprocessing function.

Interference Modeling (28)

Interference estimation and subtraction uses an independent calibration set of samples in which the interference is approximately orthogonal to the analyte signal of interest to develop a model relating the change in the measured or determined property values of the interference to changes in the spectral measurement. The model parameters may be computed using multivariate regression or discrete factor analysis.

In multivariate regression, the parameters are determined by relating the changes in the spectral information to measured property values of the interference. The resulting model is simply the multivariate regression vector. Methods such as Partial Least Squares (PLSR) and Principal Component Regression (PCR) are preferred, but other methods such as Locally Weighted Regression (LWR), Multiple Linear Regression (MLR), and Classical Least Squared (CLS) may also be applied. The regression vector, W, can be represented by the following equation $$W = g(x, y), \tag{4}$$

where $g: \Re^{N \times 2} \to \Re^N$ is the multivariate regression function, x is the preprocessed spectrum of the calibration set and y is the corresponding measured property values of the interference. The values of y could also be a target score vector determined through a principal components analysis. Given the spectrum of a new sample, x', that contains interference, the new spectrum, $\bar{x}'$, with interference removed is given by $$\bar{x}' = x'\left(I - \frac{W^T W}{\|W\|^2}\right) \tag{5}$$

where I is an appropriately scaled identity matrix and W is the regression vector of the modeled interference.

In discrete factor analysis, the signal of interference is estimated by performing an analysis of the spectral scores and loadings and then determining which factor best represents the interference. The signal is removed by reconstructing the spectrum using the spectral scores and loadings less the factor representing the interference. Principal components analysis is the preferred analytical method although other factor based methods can be easily integrated into this system. In general a set of spectra, x, with m number of samples and n wavelengths can be given by $$x = XVV^T, \tag{6}$$

where v is a n by m matrix of eigenvectors developed from a principal components analysis on the spectrum x. The resulting spectrum, $\bar{x}$, with the interference removed can be given by $$\bar{x} = x(I - v_k v_k^T) \tag{7}$$

where the $k^{th}$ column of the eigenvector matrix v represents the interference to be removed.

Sample Classification (29)

The sample classification procedure is a method for detecting samples that have similar spectral characteristics to previous samples for which the interference has already been modeled. This step is used to determine the most appropriate model for accurately estimating the interference to be removed. The preferred method is through a principal components analysis and an analysis of the spectral scores by means of a t-squared and t-squared limit computation. First a spectrum, m, is projected onto p number of eigenvectors contained in matrix o, that were previously determined through a principal components analysis on the calibration set of exemplary samples and stored on the computer system of the device. The calculation is given by:

$$xpc_o = \sum_{k=1}^{p} mo_k \qquad (8)$$

and produces the 1 by p vector of scores, $xpc_o$ where $O_k$ is the $k^{th}$ column of the matrix o. Next, the eigenvalues corresponding to the eigenvector matrix o are used to normalize the new scores vector to unit variance. The t-squared value, t, is determined according to $$t = \Sigma \overline{xpc_o} * (d-1) \qquad (9)$$

where $\overline{xpc_o}$ represents the normalized vector of scores and d is the number of samples in the calibration set. The t-squared value is a measure of how consistent the variability of spectrum m is with the exemplary set of calibration spectra. To determine if the variability is within the calibration set of samples, a t-squared limit is computed by performing an f-test with 95 percent confidence on the scores matrix of the calibration set. Spectra having a t-squared greater than the t-squared limit are not considered to have spectrally similar characteristics to those in the calibration set. The confidence limit can be optimized to suit the appropriate application.

The method above is repeated using multiple models until one passes the constraints. If the spectrum can be applied to several models, the model in which the computed t-squared value was the lowest is used. Samples that do not meet the constraints of any stored models are deemed as outliers and saved on the computer system for further analysis. Once the spectrum has been classified, the appropriate model or regression vector, W, is selected and applied to equation 5 to remove the targeted interference.

The above outlined classification procedure and the procedures described in the related U.S. Patent Application An Intelligent System for Noninvasive Blood Analyte Prediction, S. Malin, T. Ruchti, U.S. patent application Ser. No. 09/359,191 (Jul. 22, 1999) and by Khalil, supra are the preferred classification methods, although individuals skilled in the art will appreciate how other methods such as linear discriminant analysis, SIMCA, k nearest-neighbor, fuzzy classification, and various forms of artificial neural networks can be readily applied. See R. Duda, P. Hart, Pattern Classification and Scene Analysis, John Wiley & Sons, New York (1973) and J. Besdek, S. Pal, eds., Fuzzy Models for Pattern Recognition, IEEE Press, Piscataway, N.J. (1992) and C. Chen, Fuzzy Logic and Neural Network Handbook, IEEE Press, Piscataway, N.J. (1996) and L. Zadeh, Fuzzy Sets, *Information Control*, Vol. 8, pp. 338–353 (1965) and S. Haykin, Neural Networks: A Comprehensive Foundation, Prentice Hall, Upper Saddle River, N.J. (1994) and Y. Pao, Adaptive Pattern Recognition and Neural Networks, Addison-Wesley Publishing Company, Reading Mass. (1989).

Interference Subtraction Applied to the Measurement of Analytes

The method for subtracting interference from an independent set of measurements is no different from that of the calibration set. Prior to the removal of the interference in an independent set, several baseline samples are collected to characterize the interference expected in future samples. The same procedure previously described is performed on the baseline measurements to extract the interference. Once the interference is determined, a new spectral sample is collected, the newly determined interference signal is subtracted, and the analyte value measured. The measured value is expected to be biased from the true blood reference value due to the non-linearities and un-modeled synergistic effects in the data. This bias is constant for all measurements in which the sample is spectrally similar to those used in the determination of the interference. To accurately adjust the model, the mean difference between N number of blood reference values and the associated model measurements can be added to the model intercept. The outlier detection and classification procedures previously described are just a few of the methods that can be used to determine spectral similarity. Once a future sample or group of samples is considered spectrally dissimilar from the previous collected samples, the procedure defined above must be repeated.

Implementation Details

This section discloses specific procedures for targeted interference modeling and removal. The procedures are based on a-priori knowledge of the undesired spectral variance that is attributed to known sources such as skin temperature, hydration, and day-to-day changes in the mean spectrum. The parameters for each procedure, such as the eigenvectors for outlier detection and classification, are independently determined on the basis of an experimental set of exemplary data providing the required information.

Experimental Data Sets

Two data sets are disclosed to provide examples for the two methods described subsequently. A proprietary data set, based on an invented tissue phantom, that has been fully described in U.S. patent application Ser. No. 09/502,877, Intra-Serum and Intra-Gel used to Model Human Skin Tissue, K. Hazen, J. Welch, S. Malin, T. Ruchti, A Lorenz, T. Troy, S. Thenadil, T. Blank, (Feb. 10, 2000), the entirety of which is hereby incorporated herein by reference, will be used to describe interference modeling through multivariate regression. A clinical data set will be used to provide examples for interference modeling through discrete factor analysis. These data sets are described in greater detail below.

Data Set for Multivariate Regression

An INTRA-SERUM™ data set was created to provide a family of samples for which the scattering properties and absorption characteristics are closely matched to those observed in human tissue. A full description of this data set and its intended uses has been provided in U.S. patent application Ser. No. 09/502,877 supra. Selected samples have been used for the examples described herein. The data set consists of 182 absorbance spectra and corresponding concentrations for all chemical constituents. Of the 182 spectra, 175 contain unique chemistries, with the remaining seven being used as precision center-points. The data were split into calibration and testing sets with the high leverage "corner" samples being placed in the calibration set. The calibration set was used to model the interference caused by INTRALIPID, a lipid fraction of the tissue phantom, and develop a calibration for glucose. The test set was used to test the performance of each procedure and provide visual examples of the methods described subsequently.

Data Set for Discrete Factor Analysis

Fifteen human subjects of diverse age, sex, and race were recruited to participate in a study aimed at non-invasively measuring glucose. Each subject made approximately 16–20 visits to a test site, during which time their glucose levels were manipulated to give changing glucose profiles. Depending on the visit type and the rate of change in the glucose of the individual, venous blood was drawn at various times preceded by a spectral scan collected on the right forearm of each subject using the preferred embodiment. Of the fifteen subjects, three subjects produced statistically significant glucose measurement results and are used herein for the following discussion. The visits for each individual were separated into calibration and validation sets. The calibration set was used to develop the multivariate model relating the change in spectral measurement to a measured or estimated property value of the interference. The validation set was used to determine the effectiveness of the model in removing the unwanted interference from the spectral measurement and its impact on glucose measurement.

While the above experiments are aimed at increasing the robustness and accuracy of non-invasive analyte measurement, one skilled in the art will readily appreciate its application to any system where known interference causes a reduction in the net analyte signal of interest.

Method 1—Interference Modeling Through Multivariate Regression

The first method models the known interference by regressing the NIR spectral data 30 against the measured property values of the interference. An exemplary set of calibration spectra 31 and measured property values of the interference 32 are used to develop a multivariate model 33 relating the change in a spectrum to a single property value. The basis for this method is that differences in the properties and characteristics of the unwanted interference (i.e. temperature, pathlength, etc.) cause systematic variation in the absorbance spectrum that can be modeled using multivariate statistical methods. To avoid modeling synergistic effects in the spectra related to the desired chemical constituents, the interfering signal must be orthogonal to the analyte signal of interest. Although the method as described employs Principal Component Regression (PCR), other factor-based multivariate regression methods can be readily applied.

Principal Component Regression (33)

Figure 2:
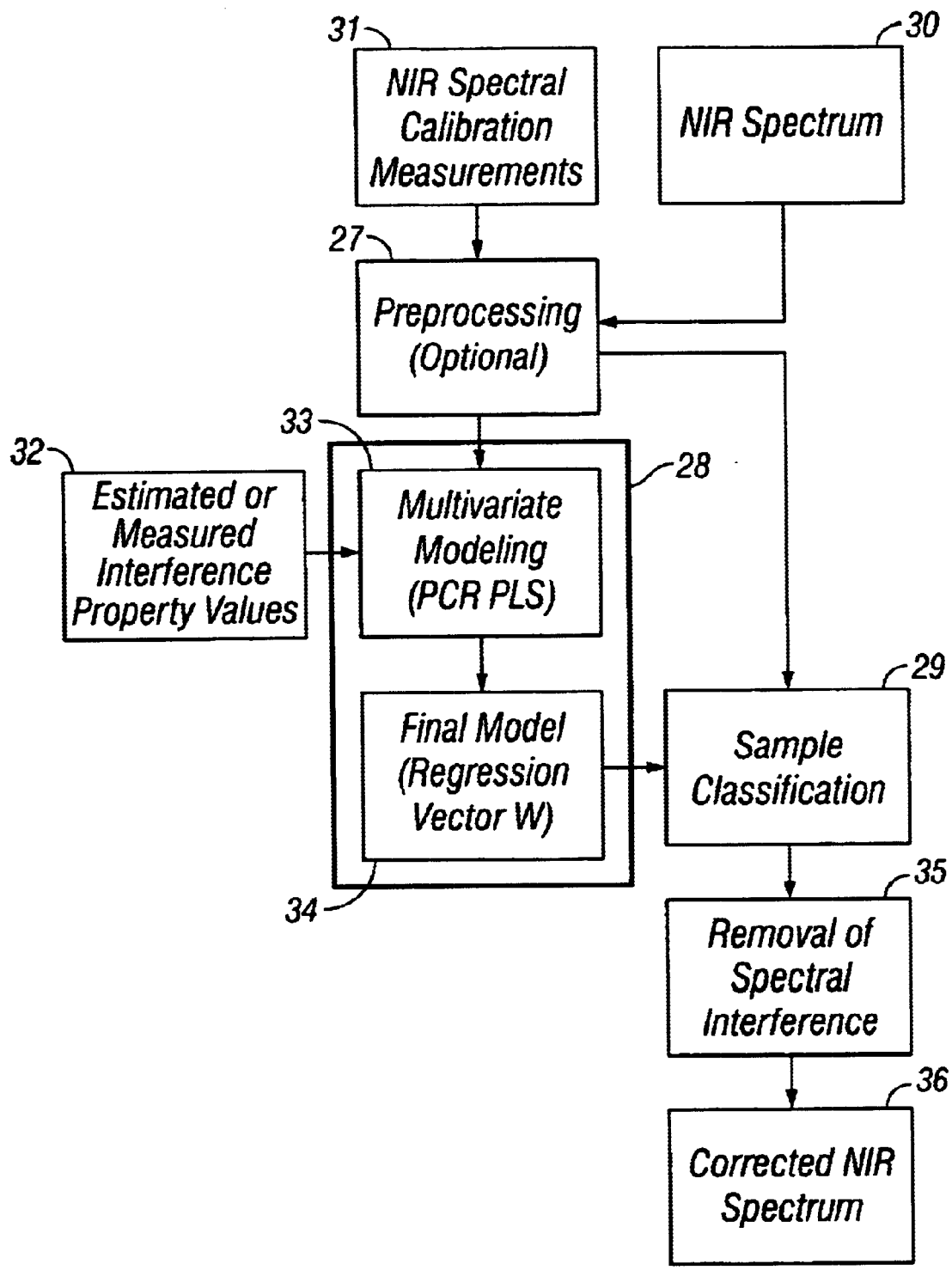
FIG. 2 provides a block diagram of a procedure for modeling and subtracting interference using multivariate regression according to the invention.
Figure 3:
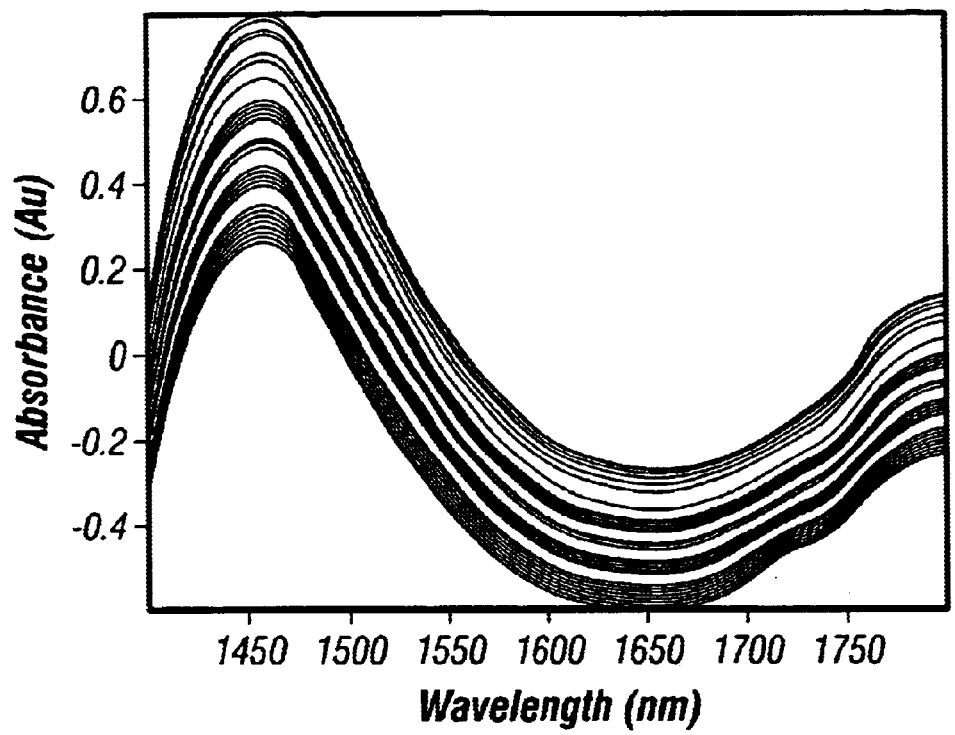
FIG. 3 shows plots of NIR absorbance spectra of selected samples from a sample data set derived from a tissue phantom according to the invention.

The general procedure utilizing this method is shown in FIG. 2. First, the NIR spectral data 30 such as those shown in FIG. 3 are measured using the preferred embodiment of the apparatus previously described. The collected spectrum, x, contains n number of samples by p number of wavelengths and is used in a subsequent principal components analysis (PCA) to generate a n by 1 vector of eigenvalues and a p by n eigenvector matrix. Eigenvalues and eigenvectors are computed using Singular Value Decomposition (SVD), which is used in PCA and other calibration methods. See H. Martens, T Naes, *Multivariate Calibration*, John Wiley & Sons, Ltd., New York, (1989) pp. 96–116. The regression vector W(34), is related to the spectral data, x, and interference property values, y, by $$U = V^T x \text{ and} \quad (10)$$

$$W = y U^T inv(UU^T) V^T, \quad (11)$$

where V is a matrix containing a selected number of eigenvectors. The predicted property values of the interference are given by $$\bar{y} = xW - b, \quad (12)$$

where $\bar{y}$ is the predicted value and b is the mean of measured property values of interference in the exemplary set of calibration data. The number of factors or eigenvectors used to represent the interference can be determined through cross-validation on the calibration sample set or through an independent set of test samples by iteratively increasing the number of factors used to develop the model and minimizing the standard error in prediction (SEP). The SEP is given by $$SEP = \sqrt{\frac{1}{n} \sum_{k=1}^{n} (y_k - \bar{y}_k)^2} \quad (13)$$

where n is the number of total predicted samples and the subscript k denotes the $k^{th}$ sample. The preferred method for optimizing the regression model is to use an independent sample set because it provides a more robust estimation of the interference. The acceptability of the model is based on a F-Test, which is the ratio of the squared SEP over the variance in the measured property values. Once the model has been developed, the selected eigenvector matrix, V, and regression vector, W, are stored on the computer system of the device and used to estimate the interference of a new sample spectrum. The interference is removed 35 by applying the resulting model 34 and the new spectrum to equation 5, resulting in a corrected spectrum 36.

Figure 4:
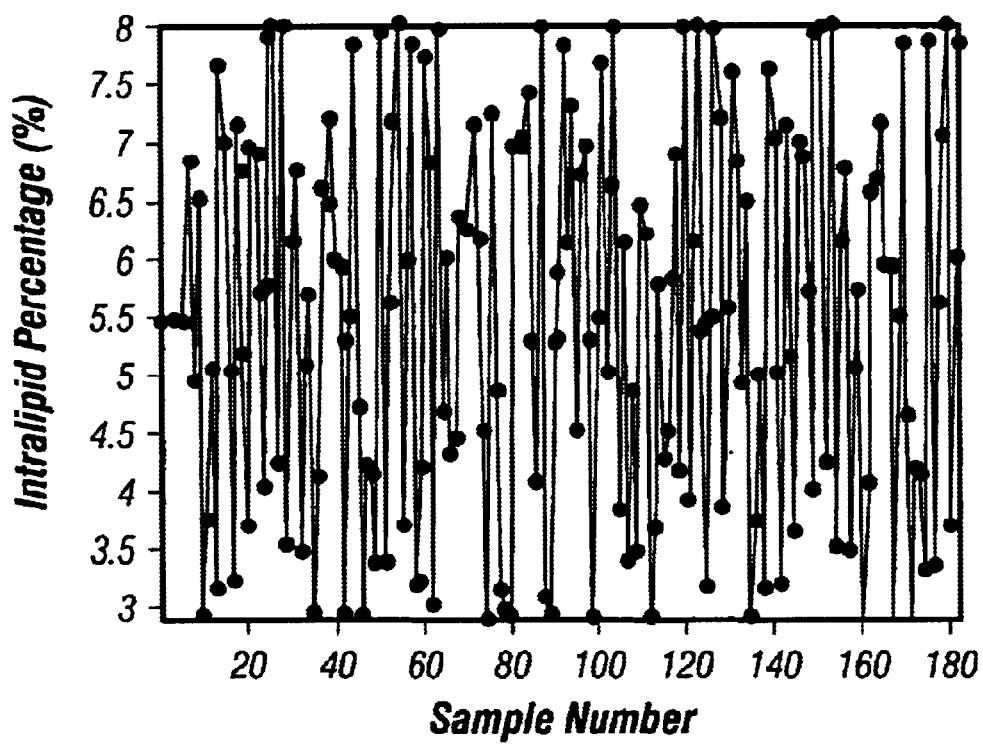
FIG. 4 is a graph of percentages of a lipid fraction present in the samples of the sample data set of FIG. 3 according to the invention.
Figure 5:
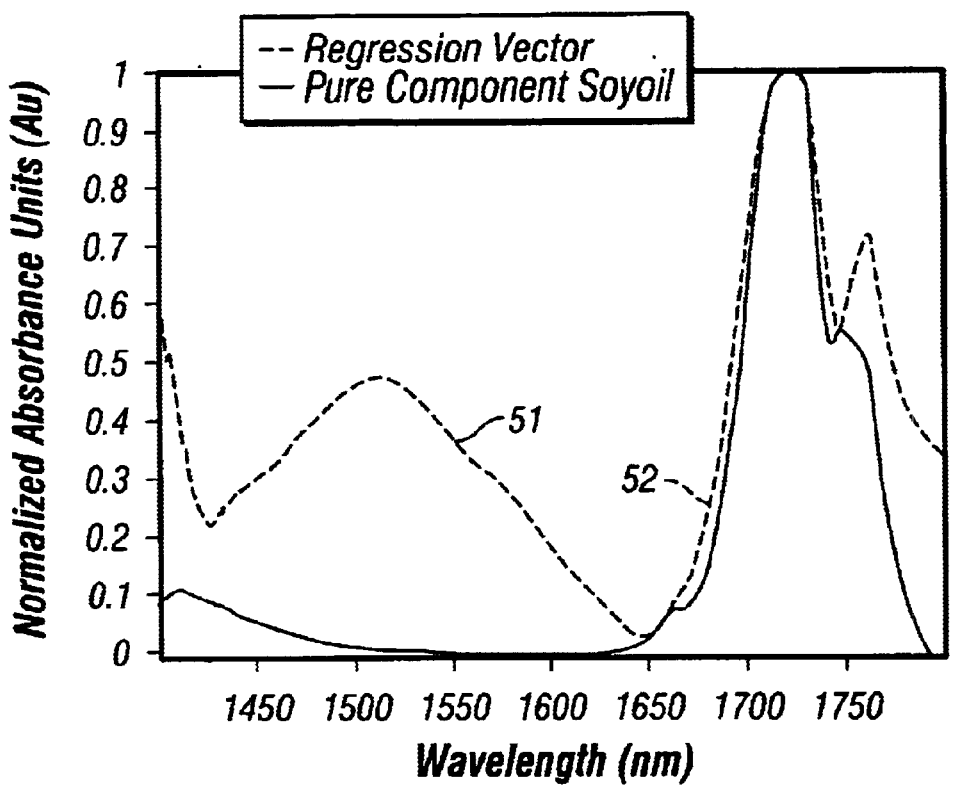
FIG. 5 provides a plot of a normalized regression vector derived by modeling the lipid fraction of FIG. 4 over a normalized pure component spectrum of soy oil according to the invention.

For example, consider a set of diffuse reflectance absorbance spectra with corresponding INTRALIPID percentages plotted in FIGS. 3 and 4, respectively. The data are evenly split into independent calibration and testing sets. A Principal components analysis is performed on the calibration spectra to produce an eigenvector matrix. Starting with one factor or eigenvector, the regression vector relating the change in the spectral data to INTRALIPID percentage is computed using equations 10–11. Equations 12 and 13 can then be used to predict the INTRALIPID percentages and compute the SEP in the independent test set. The resulting SEP is the error in the model from using one factor. In an iterative manner, the number of factors or eigenvectors in V are increased by one, the regression model is developed, and the SEP is computed until all eigenvectors from the initial PCA model are included in V. The SEP is plotted versus the number of eigenvectors and the number of factors is determined that provides the best estimate of the interference with the least number of factors. In other words, it is important not to over estimate the interference by choosing "n" number of factors when "n–5" number of factors gives a comparable result. From plotting the normalized regression vector 51 over the pure-component spectra of soy oil (the major component in INTRALIPID) 52 in FIG. 5, it is apparent that the primary absorbance feature in the pure component spectrum is accounted for in the resulting model.

Figure 6:
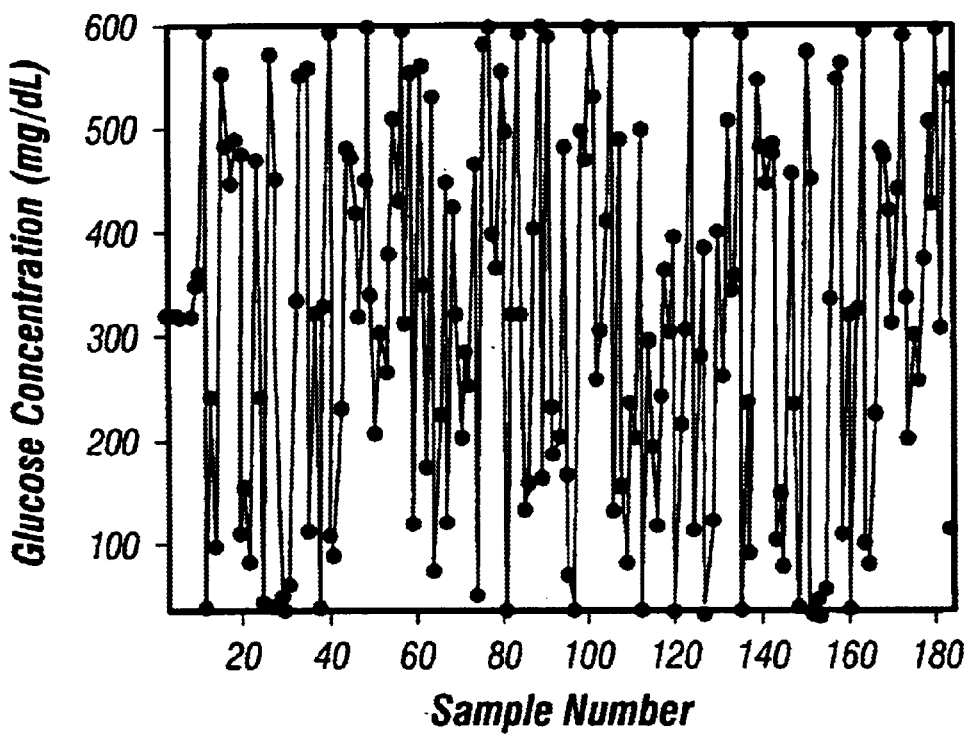
FIG. 6 shows a graph of measured glucose concentrations in the sample data set of FIG. 3 according to the invention.
Figure 7:
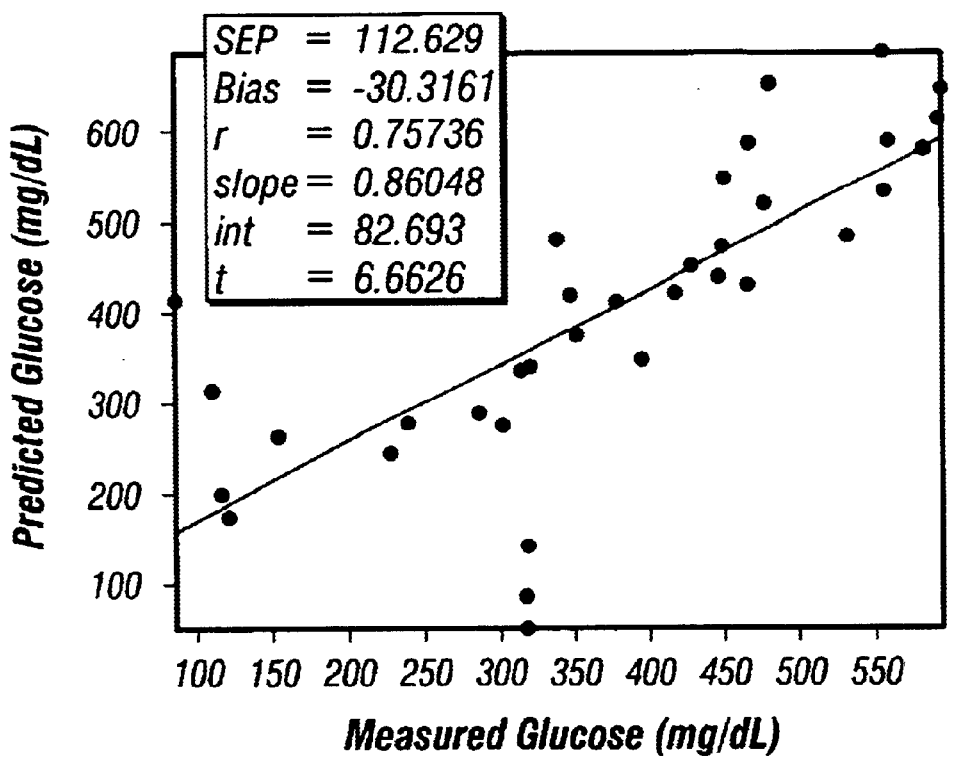
FIG. 7 shows a plot of actual vs. predicted glucose concentration in the sample data set of FIG. 3 prior to removal of the Net Analyte Signal of the lipid fraction of FIG. 4 according to the invention.
Figure 8:
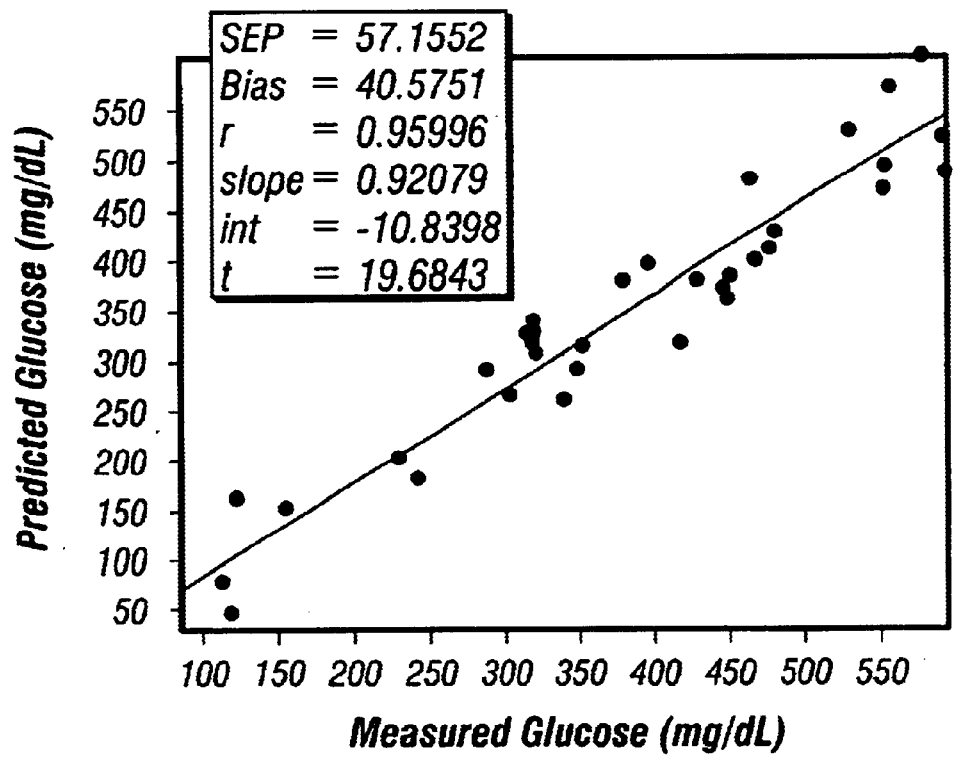
FIG. 8 shows a plot of actual vs. predicted glucose concentration in the sample data set of FIG. 3 after removal of the Net Analyte Signal of the lipid fraction of FIG. 4 according to the invention.
Figure 9:
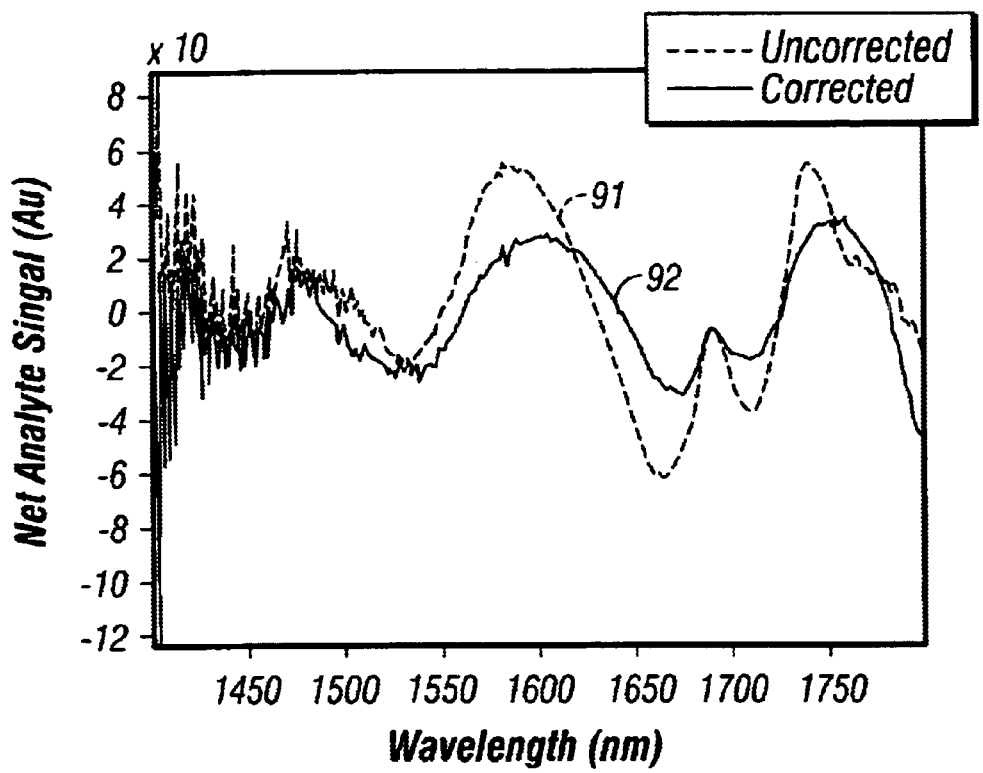
FIG. 9 shows a Net Analyte Signal estimated from a calibration model before and after removing the Net Analyte Signal of the lipid fraction of FIG. 4 according to the invention.

To illustrate the removal of the interference caused by INTRALIPID, the absorbance spectra previously described and the corresponding glucose concentrations shown in FIG. 6 will be used. In the general case, the spectra must be preprocessed in the same manner as the calibration set. However, for this example, no preprocessing was applied. Next, the interference is removed by applying the absorbance spectra and the regression vector from the INTRALIPID model to equation 5. Using the same calibration and testing sets described above, glucose calibrations were performed on the uncorrected and interference corrected absorbance spectra. FIGS. 7 and 8 display measured versus the predicted glucose concentrations prior to and after removal of the interference, respectively. The glucose SEP has effectively been reduced by half. Plotted in FIG. 9 is the Net Analyte Signal (NAS) of glucose in the models generated from the corrected and uncorrected absorbance spectra.

This plot illustrates that the model generated using the uncorrected spectra includes information pertaining to INTRALIPID, resulting in an increase in the glucose SEP.

Method 2—Discrete Factor Analysis

In discrete factor analysis, the signal of interference is estimated by performing an analysis of the spectral scores and loadings and determining which factor best represents the interference. In factor-based methods like PCA, each factor (eigenvector) represents a different type of variation observed in the spectra. Most factors are not variations caused by a single source, but rather a sum of variations from many different sources. If the magnitude of spectral variation from a single source is large, it may discretely comprise one factor. The basis for this method is that if a factor can discretely comprise one variation source or the majority of one source, it can be removed 65 by reconstructing the spectra using all factors less the factor with the interference. Although principal components analysis (PCA) has been used in the subsequent section, other factor-based multivariate methods may be readily applied.

Figure 10:
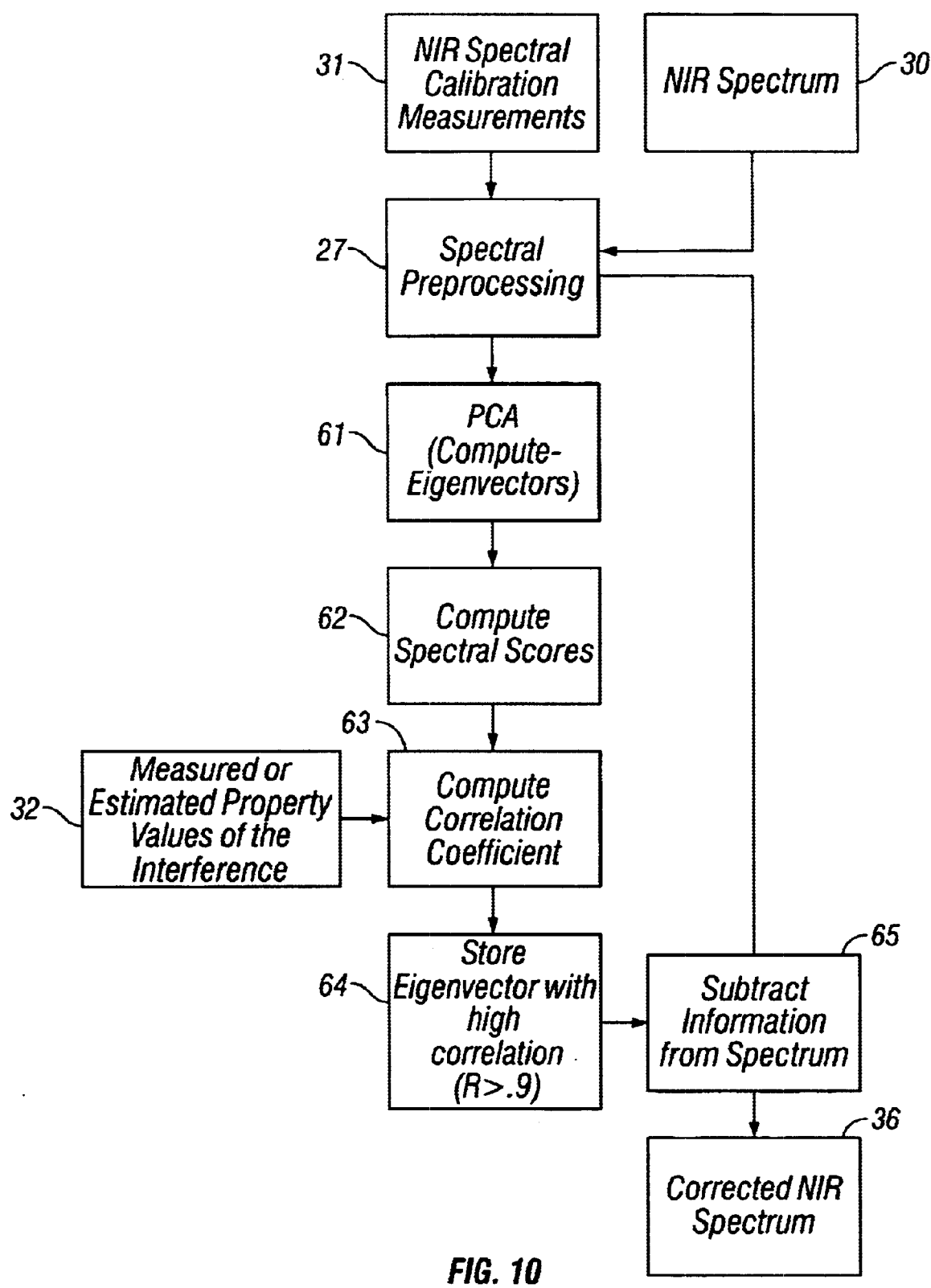
FIG. 10 provides a block diagram of a procedure for subtracting spectral interference based on discrete factor analysis according to the invention.
Figure 11:
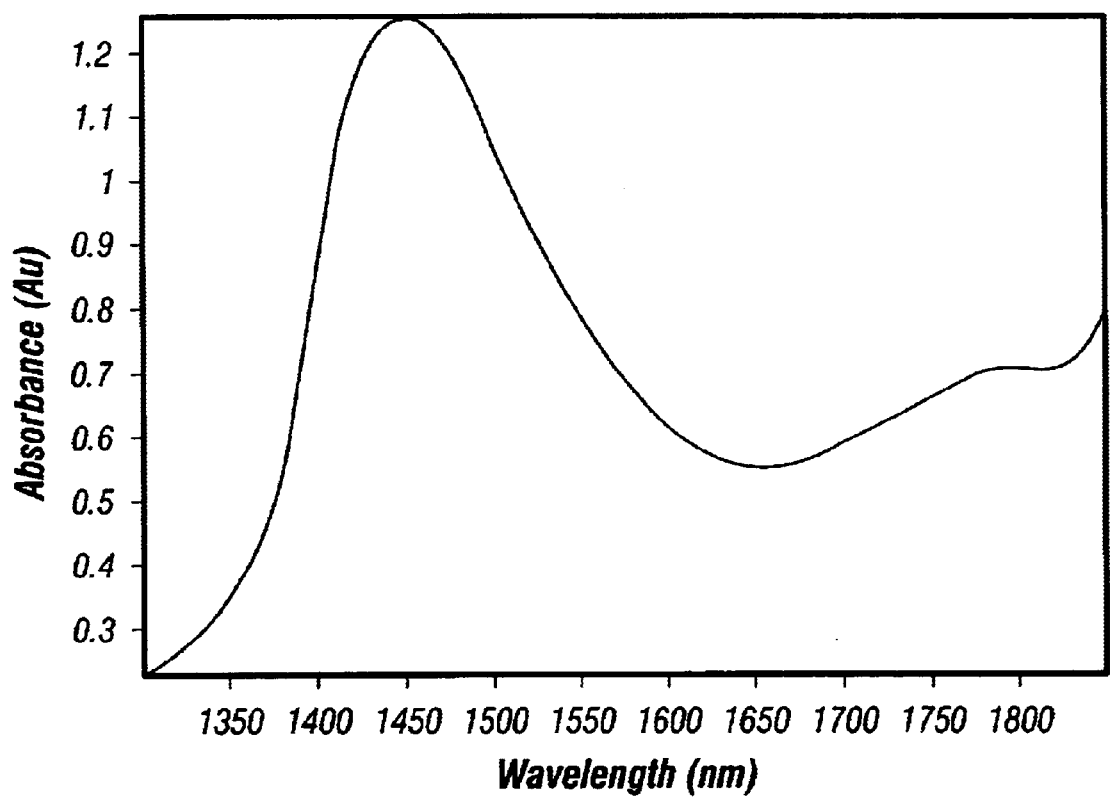
FIG. 11 shows a typical NIR absorbance spectrum collected from the forearm of a test subject according to the invention.

FIG. 10 presents a block diagram of a general procedure based on this method. First, absorbance spectra 18 such as the spectrum shown in FIG. 11, are measured using the preferred embodiment. The collected spectra, x, contains n number of samples by p number of wavelengths and is used in a subsequent Principal components analysis 61 (PCA) to generate a n by 1 vector of eigenvalues and a p by n eigenvector matrix. Eigenvalues and eigenvectors are computed using Singular Value Decomposition (SVD), commonly used in PCA and other factor-based multivariate methods. See Martens, et al., supra. The spectral scores 62, T, are given by $$T = xV \quad (14)$$

where V is a p by n eigenvector matrix. Either the scores or the eigenvectors can be used to determine the source of variation. If the shape or the general variation at each wavelength manifested by the interference is known, the eigenvectors can be analyzed for similar shape and variation. If there are corresponding property values of the interference or the magnitude of the interference is known, the spectral scores can be analyzed for similar changes in magnitude 63. Once the factor that represents the interference has been determined, the corresponding eigenvector is then stored 64 on the computer system of the device. Future samples can be corrected by applying the stored eigenvector, v, to equation 7.

Figure 12:
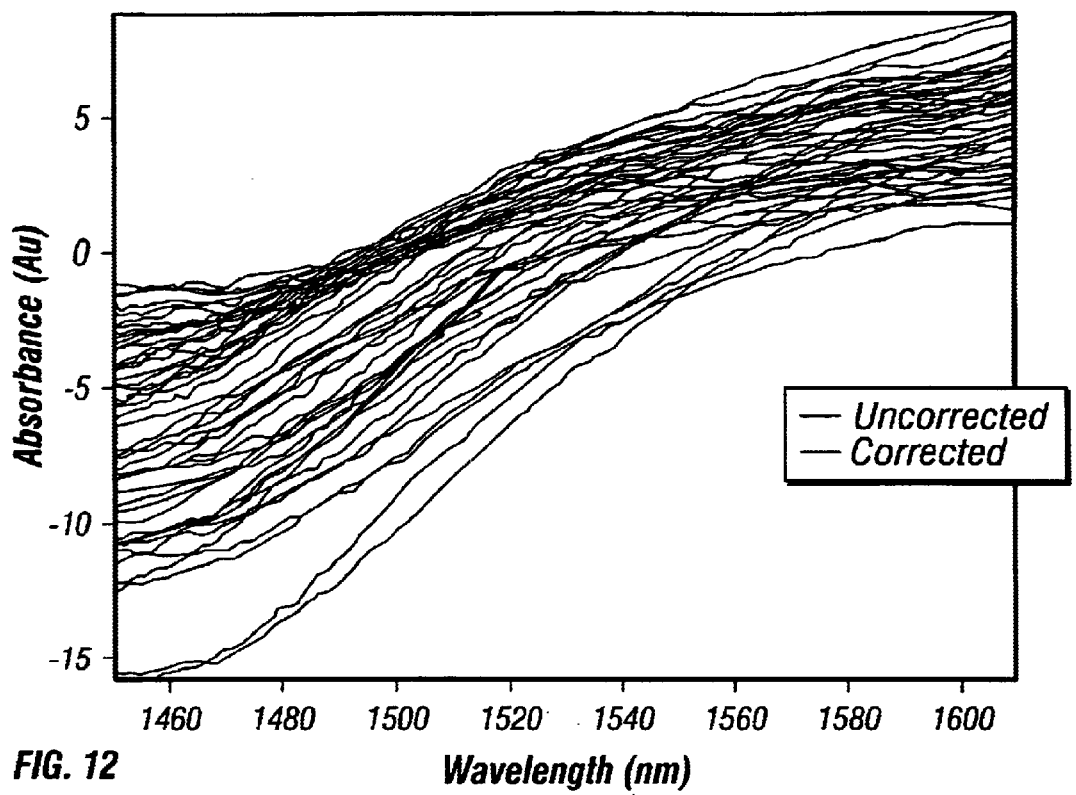
FIG. 12 shows the wavelength region 1450–1600 nm of mean-centered spectra prior to and after removal of first factor information according to the invention.
Figure 13:
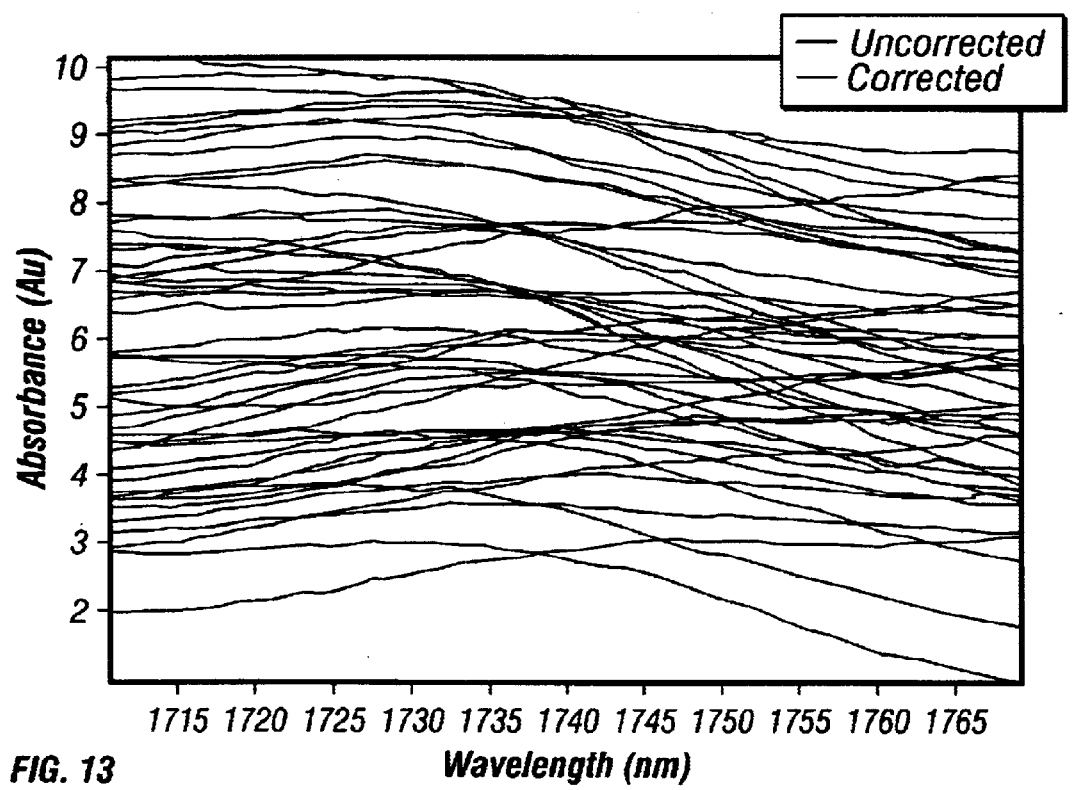
FIG. 13 shows the wavelength region 1710–1770 nm of mean-centered spectra prior to and after removal of first factor information according to the invention.

By way of example, clinical data are provided for a single subject containing absorbance spectra, such as that shown in FIG. 11, along with corresponding glucose concentrations. According to visit, the data are split into independent calibration and testing sets. A principal components analysis is performed on the calibration spectra to produce an eigenvector matrix 61. The spectral data and resulting eigenvector matrix are used to compute the spectral scores 62 using equation 14. Analysis of the first factor principal component scores reveals that the information comprising the first eigenvector is related to multiple effects attributable to varying hydration, changes in the sampled tissue, and changes in the mean spectrum unrelated to glucose. The information in the spectra related to the first eigenvector can be removed 65 by its application to equation 7. Generally, future samples can be also corrected 36 by applying the same preprocessing as performed on the calibration data set (none in this case) and subtracting the information using equation 7. Plotted in FIGS. 12 and 13 are the independent test set spectra with and without the first factor information in the two specific regions needed for glucose measurement, respectively. These two figures clearly illustrate a change in the signal due to the removal of the information represented in the first factor.

Figure 14:
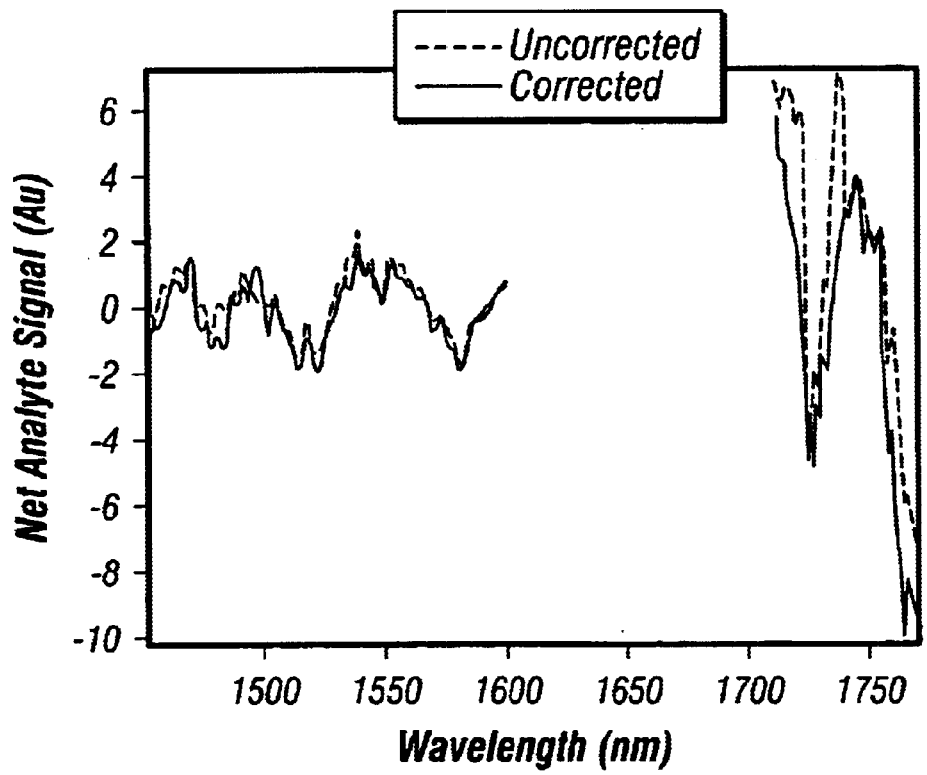
FIG. 14 shows the Net Analyte Signal of glucose for a single test subject estimated from a calibration model prior to and following the removal of the first factor determined from a principle components analysis on the calibration data set.

The previously described methodology was applied to three different subjects with the objective of increasing glucose calibration robustness and accuracy. The calibration set for each subject was used to model the discrete factor of interference and develop the model for glucose measurement. The test sets were used to determine the impact on glucose measurements of removing the first factor information from the spectral data. Plotted in FIG. 14 is the Net Analyte Signal of glucose prior to and after the removal of the first factor. This figure illustrates that the spectral signal changed after removal of the first factor, with the biggest impact occurring in the 1710–1770 nanometer region of the spectra. Table 1 summarizes the calibration results obtained from applying this method to the non-invasive spectra of three different subjects. In all cases, the SEP improved after removal of the first factor. The results clearly indicate that every measurement result improved in accuracy upon removal of the first factor. Additionally, the total number of factors used in the generation of the glucose model decreased by at least one (which is expected since one is being removed) in every example, indicating an increase in calibration robustness.

The foregoing description is exemplary only and not intended to be limiting. The described examples are illustrative of how the invented methods may be applied to remove unwanted spectral variation and increase calibration accuracy. Those skilled in the art will readily appreciate how these methods can be applied to any spectral measurement in which interfering signals inhibit the chances of developing robust calibration models for measuring trace levels of biological constituents. Furthermore, sample classification can be used to determine the appropriate model to best estimate the signal of interference based on the similarities between the new spectral sample and the samples used to develop the classification models stored on the computer system of the device.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. An apparatus for modeling and removing targeted interfering signals from spectral measurements comprising:
   means for measuring a spectrum of a sample;
   at least one interference model, wherein said interference is approximately orthogonal to an analyte signal of interest, said interference model adapted to remove spectral interference from said measured spectrum; and
   means for selecting most appropriate interference model for estimating interference to be removed from said measured spectrum.

2. The apparatus of claim 1, wherein said apparatus is adapted to measure a spectrum of a tissue sample noninvasively.

3. The apparatus of claim 1 wherein said means for measuring a spectrum comprises:
   a radiation source;
   means for coupling radiation to the sample;

means for collecting radiation that is any of diffusely scattered and transmitted from the sample;

means for dispersing said collected radiation;

means for detecting said dispersed radiation at predetermined bands of wavelengths and converting said detected radiation to a proportional voltage; and means for digitizing said voltage.

4. The apparatus of claim 3, wherein said radiation source comprises a broadband light source.

5. The apparatus of claim 3, further comprising a band pass filter, said band pass filter adapted to limit radiation reaching said sample to a targeted wavelength range.

6. The apparatus of claim 3, said apparatus further comprising a blocking element, said blocking element adapted to intermittently block transmission of radiation toward said sample so that any of a baseline and a detector dark current can be detected.

7. The apparatus of claim 3, wherein said means for coupling radiation to said sample comprises at least one fiber optic and a focusing element.

8. The apparatus of claim 3, wherein said means for collecting light comprises at least one fiber optic.

9. The apparatus of claim 3, further comprising a probe, said probe adapted to establish contact of said means for coupling light and said means for collecting light with surface of said tissue sample.

10. The apparatus of claim 3, wherein said means for dispersing collected radiation comprises a grating.

11. The apparatus of claim 3, further comprising a coupling element adapted to couple said means for collecting radiation to an aperture, said aperture adapted to directed radiation toward said means for dispersing radiation.

12. The apparatus of claim 11, wherein said aperture comprises a slit.

13. The apparatus of claim 3, wherein said means for detecting radiation comprises a detector array with associated amplifiers, said array and said amplifiers adapted to convert said detected radiation to a voltage proportionate to a detected signal.

14. The apparatus of claim 3, wherein said means for digitizing said voltage comprises an analog-to-digital converter.

15. The apparatus of claim 1, wherein said interference model is calculated from one or more calibration sets.

16. The apparatus of claim 1, wherein said interference model estimates interference based on one of:

multivariate modeling, wherein known interference is modeled by regressing spectral data against measured property values of the interference; and discrete factor analysis, wherein interference is estimated by performing an analysis of spectral scores and loadings and determining which factor best represents the interference; and wherein signal is removed by reconstructing the spectrum using the spectral scores and loadings less the factor representing the interference.

17. The apparatus of claim 1, said means for selecting most appropriate interference model comprising a processing element, wherein said processing element is programmed to execute a sample variability classification procedure, wherein most appropriate interference model is selected for estimating interference to be removed from said measured spectrum.

18. The apparatus of claim 1, wherein said at least one interference model comprises a plurality of interference models.

19. A method for estimating and removing spectral interference from a measured spectrum comprising the steps of:

providing one or more calibration sets of exemplary spectral measurements and corresponding measured property values;

providing one or more spectral measurements, each of said measurements comprising a sample;

calculating one or more interference models from said one or more calibration sets, wherein said interference is approximately orthogonal to an analyte signal of interest;

selecting most appropriate interference model for estimating interference to be removed;

estimating said interference; and removing said interference from said sample.

20. The method of claim 19, wherein said spectrum is denoted by a vector $m \in \Re^N$ of absorbance values pertaining to a set of N wavelengths $\lambda \in \Re^N$.

21. The method of claim 19, wherein said measurements are in the wavelength region 700–2500 nm, said wavelength region corresponding to the near infrared (NIR).

22. The method of claim 19, further comprising the step of:

detecting outliers, wherein said outliers are invalid measurements caused by spectral variations due to any of instrument malfunction, poor sampling of a subject and subjects outside of the calibration set.

23. The method of claim 22, wherein said outlier detection step employs principal components analysis and analysis of resulting residuals to detect spectral outliers.

24. The method of claim 23, wherein said outlier detection step comprises the steps of:

projecting a spectrum m onto five eigenvectors contained in a matrix o, said matrix o being previously developed through a principal components analysis of said calibration set, where $$xpc_o = \sum_{k=1}^{5} mo_k,$$

$xpc_o$ being a 1 by 5 vector of scores and where $O_k$ is the $k^{th}$ column of the matrix o;

determining the residual q, according to $$q = m - xpc_o o^T;$$

comparing said residual q to three times the standard deviation of the residual of said calibration set; and reporting said sample as an outlier if q is greater than three times the standard deviation of the residual of said calibration set.

25. The method of claim 19, further comprising the step of:

preprocessing, wherein said preprocessing step includes one or more transformations that attenuate noise and instrumental variation without affecting a signal of interest.

26. The method of claim 25, wherein a preprocessed measurement, $x \in \Re^N$, is determined according to:

$$x = h(\lambda, m),$$

where h: $\Re^{N \times 2} \to \Re^N$ is a preprocessing function.

27. The method of claim 19, wherein parameters of said interference models are calculated using multivariate regression and wherein a resulting model comprises a multivariate regression vector.

28. The method of claim 27, wherein said multivariate regression vector is computed using one of:
Partial Least Squares (PLSR);
Principal Component Regression (PCR);
Locally Weighted Regression (LWR);
Multiple Linear Regression (MLR); and
Classical Least Squared (CLS).

29. The method of claim 28, wherein said regression vector is computed using Principal Component Regression.

30. The method of claim 29, wherein a Principal Components analysis is performed on one or more spectral measurements, wherein the collected spectra, x contain n number of samples by p number of wavelengths.

31. The method of claim 30, wherein a n by 1 vector of eigenvalues and a p by n eigenvector matrix is computed using Singular Value Decomposition.

32. The method of claim 31, wherein said regression vector, W, is related to said spectral measurements, x, and interference property values, y, by:

$$U=V^T x \text{ and}$$

$$W=yU^T inv(UU^T)V^T,$$

where V is a matrix containing a selected number of eigenvectors.

33. The method of claim 32, wherein predicted property values of the interference are given by:

$$\bar{y}=xW+b,$$

where $\bar{y}$ is the predicted value and b is the mean of the measured property values form the calibration set.

34. The method of claim 33, wherein the number of factors, said factors comprising eigenvectors, representing said interference is determined through cross validation on one of the calibration set and an independent set of test samples by iteratively increasing the number of factors used to develop the model and minimizing the standard error of prediction (SEP).

35. The method of claim 34, wherein the SEP is given by:

$$SEP = \sqrt{\frac{1}{n}\sum_{k=1}^{n}(y_k - \bar{y}_k)^2},$$

where N is the number of total predicted samples and the subscript k denotes the $k^{th}$ sample.

36. The method of claim 35, wherein acceptability of the model is based on an F-test, wherein said F-test is the ratio of the squared SEP to the variance in the measured property values.

37. The method of claim 31, wherein said eigenvector matrix V and said regression vector W are saved and used to estimate interference of new sample spectra.

38. The method of claim 27, wherein said regression vector, W, is represented by:

$$W=g(x,y),$$

where g: $\Re^{N \times 2} \rightarrow \Re^N$ is the multivariate regression function, x is the preprocessed spectra of the calibration set and y is one of the corresponding measured property values of the interference and a target score vector determined through principal components analysis.

39. The method of claim 38, wherein for a new sample $x$, said new sample containing interference, a new spectrum $\bar{x}$, with interference removed is given by:

$$\bar{x}' = x'\left(I - \frac{W^T W}{\|W\|^2}\right),$$

where I is an appropriately scaled identity matrix and W is the regression vector of the modeled interference.

40. The method of claim 19, wherein parameters of said interference models are calculated using discrete factor analysis.

41. The method of claim 40, wherein a signal of interference is estimated by performing an analysis of spectral scores and loadings and determining which factor best represents the interference.

42. The method of claim 41, wherein said signal of interference is removed from said measured spectrum by reconstructing said spectrum using said spectral loadings and scores minus the factor representing the interference.

43. The method of claim 42, wherein said interference modeling step employs one of principal components analysis and another factor-based analytical method.

44. The method of claim 43, wherein a set of spectra x, having m number of samples and n wavelengths is given by:

$$x=xvv^T,$$

where v is a n by m matrix of eigenvectors developed from a principal components analysis on the spectra x.

45. The method of claim 43, wherein spectra $\bar{x}$, having said interference removed, are given by:

$$\bar{x}=x(I-v_k v_k^T),$$

where the $k^{th}$ column of the eigenvector matrix v represents the interference to be removed.

46. The method of claim 43, wherein a set of spectra, x, having n number of samples by p number of wavelengths are used in a principal components analysis to generate a n by 1 vector of eigenvalues, and a p by n eigenvector matrix.

47. The method of claim 46, wherein said eigenvectors and eigenvalues are computed using Singular Value Decomposition.

48. The method of claim 46, wherein spectral scores, T, are given by:

$$T=xV,$$

where V is a p by n eigenvector matrix, and wherein one of spectral scores and the eigenvectors are used to determine a variation source.

49. The method of claim 48, wherein said eigenvectors are analyzed for shape and variation similarities with shape and variation manifested at each wavelength where the interference is known.

50. The method of claim 48, wherein spectral scores are analyzed for similar changes in magnitude where there are corresponding property values for said interference or if the magnitude of the interference is known.

51. The method of claim 48, wherein a corresponding eigenvector is stored wherein a factor corresponding to said interference is known, and wherein said stored eigenvector is used to correct future samples.

52. The method of claim 19, wherein the step of selecting most appropriate interference model for estimating interference to be removed comprises:
classifying samples, wherein a sample is compared to other samples for which interference has already been modeled so that the most appropriate interference model is selected for estimating interference to be removed.

53. The method of claim 52, wherein said sample classification step comprises a principal components analysis of said sample and an analysis of spectral scores through t-squared and t-square limit computation.

54. The method of claim 53, wherein a spectrum m is projected onto p number of eigenvectors contained in a matrix o previously determined through a principal components analysis on said calibration set, where the calculation is given by:

$$xpc_o = \sum_{k=1}^{p} mo_k,$$

so that a 1 by p vector of scores, $xpc_o$ is produced, where $o_k$ is the $K^{th}$ column of the matrix o.

55. The method of claim 54, wherein eigenvalues corresponding to said eigenvector matrix o are used to normalize new scores to unit variance.

56. The method of claim 55, wherein a t-squared value, t, is determined according to:

$$t = \Sigma \overline{xpc_o} * (d-1),$$

where $\overline{xpc_o}$, represents a normalized vector of scores and d is the number of samples in said calibration set, and wherein said t-squared value is a measure of how consistent variability of said spectrum m is with said calibration set of exemplary spectra.

57. The method of claim 56, wherein a t-squared limit is computed by performing an f-test with a confidence limit on the scores matrix of said calibration set so that a sample having a t-squared value exceeding said t-squared limit is considered to have spectral characteristics dissimilar to those in the calibration set, and wherein said confidence limit is optimized according to the application.

58. The method of claim 57, wherein said confidence limit is ninety-five percent.

59. The method of claim 58, wherein said t-squared value is compared to t-square limits for multiple interference models until at least one passes the constraints.

60. The method of claim 59, wherein the model having the lowest t-squared limit is applied to a sample that fits several models.

61. The method of claim 60, wherein a sample failing to meet the constraints of any stored models is classified as an outlier.

62. The method of claim 52, wherein said calculating and classifying steps are based on any of:

linear discriminant analysis;

SIMCA;

k nearest neighbor;

fuzzy classification; and artificial neural networks.

63. The method of claim 19, wherein an appropriate model or regression vector is selected and applied to said sample to remove targeted interference.

64. The method of claim 63, wherein removing said interference comprises subtracting it from said sample.

65. The method of claim 19, wherein said step of estimating said interference comprises:

collecting a plurality of baseline samples removing interference from said baseline samples.

66. The method of claim 65, further comprising the step of:

subtracting interference calculated from said baseline samples from a sample measurement.

67. The method of claim 66, further comprising the step of measuring an analyte value from said sample measurement.

68. The method of claim 67, wherein measurement of said analyte value is biased from a true blood reference value due to non-linearities and un-modeled synergistic effects in data; and wherein said bias is constant for all sample measurements that are spectrally similar to said baseline samples; further comprising the step of adjusting an interference model by adding mean difference between N number of blood reference values and associated model measurements to an intercept of said model.

* * * * *